United States Patent [19]

Hulon

[11] Patent Number: 4,889,249

[45] Date of Patent: Dec. 26, 1989

[54] URINE BOTTLE WITH CAP

[76] Inventor: Walter C. Hulon, P.O. Box 40745, Baton Rouge, La. 70835

[21] Appl. No.: 213,710

[22] Filed: Jun. 30, 1988

[51] Int. Cl.$^4$ ............................................. B65D 41/34
[52] U.S. Cl. ..................................... 215/230; 4/144.1; 73/427; 215/365
[58] Field of Search ................. 215/230, 252, 365, 31; 4/144.1, 144.2; 73/427, 864.91

[56] References Cited

U.S. PATENT DOCUMENTS

| | | | |
|---|---|---|---|
| 1,797,433 | 3/1931 | McCrea | 215/11.1 |
| 2,770,382 | 11/1956 | Ritter | 215/31 |
| 3,831,453 | 8/1974 | McWhorter | 73/427 |
| 4,094,648 | 6/1978 | Seeley | 73/427 |
| 4,111,322 | 9/1978 | Obrist et al. | 215/230 |
| 4,174,783 | 11/1979 | Abe et al. | 215/1 C |
| 4,176,412 | 12/1979 | Peterson | 4/144.1 |
| 4,332,012 | 3/1982 | Conti | 215/252 X |
| 4,346,812 | 8/1982 | Banich | 215/352 |
| 4,573,601 | 3/1986 | Berglund | 215/252 |
| 4,595,110 | 6/1986 | Herr | 215/252 |

FOREIGN PATENT DOCUMENTS 2033350 5/1980 United Kingdom ................ 215/252

Primary Examiner—Donald F. Norton
Attorney, Agent, or Firm—Harrison & Egbert

[57] ABSTRACT

A urine bottle comprising a body having an internal volume for receiving urine specimens, a neck portion integrally formed with the body, and a cap threadedly connected to an exterior thread on the neck portion. The neck portion defines the mouth of the urine bottle and has an exterior thread extending therearound. The cap forms a liquid-tight seal against the mouth. The cap includes a detachable collar extending at the bottom of the cap. The detachable collar separates from the cap upon the removal of the cap from the neck portion. The neck portion further includes a ring formed outwardly of the neck portion and having a flat lower edge. The detachable collar has a plurality of inward flaps extending upwardly from the bottom of the collar. The flaps are arranged so as to engage the flat lower edge of the ring. The cap has identification information laser-encoded onto the exterior top surface of the cap. A plurality of graduated markings are formed on the exterior surface of the body.

17 Claims, 4 Drawing Sheets

URINE BOTTLE WITH CAP

TECHNICAL FIELD

The present invention relates to bottles, vessels, and containers specifically designed for the receipt, shipment, and use of urine specimens.

BACKGROUND ART

In recent years, urine testing has played a great role in the diagnosis of disease, in the analysis of health conditions, and in the testing of drug use. In the typical process of urine testing, the urine specimen is collected in a bottle at a medical facility and, then, it is shipped to a laboratory for testing. The test results are then returned to the medical facility.

The urine is examined by inspection as to its color which may be light or very dark from jaundice, breakdown of hemoglobin, or the dispersion of red cells through it. It may contain gravel, quartz, pus, microorganisms, and crystals. The specific gravity is important as a measure of the concentration of the urine. The volume of urine is important also, particularly when there is any impairment of kidney function or any obstruction. Among chemicals that may be tested in the urine are the sugars, acetone (suggestive of diabetes), various nitrogen compounds, hemoglobin and myoglobin (oxygen-carrying proteins of the blood and muscle), homogentisic acid (present in the hereditary disease alkaptonuria), coproporphyrins (suggestive of lead poisoning), prophobilinogen (present in the metabolic disease prophyria), and urea and uric acid. Enzymes and hormones are tested for. A great variety of drugs can be detected in the hormones are tested for. A great variety of drugs can be detected in the urine; these are important in cases of overdosage, sensitivity, or suicidal attempts. Urobilinogen is the important bile derivative tested for chemically. Its high secretion suggests liver disorder; its absence, bile duct obstruction. Phenolsulfonphthalein concentration in the urine after intravenous injection is a good test of kidney function. Among the minerals tested for, calcium, phosphorus, copper, and lead, are perhaps the most important.

In the past, collection and shipping have been major problems in the use of urine specimens. Important considerations in urine testing include the ability to maintain the chain of custody, accuracy in matching test results with specimen samples, tamper resistance, and prevention of contamination. Since the urine specimen passes through many hands between the time of collection and the time of report, it becomes very difficult to maintain the chain of custody. The chain of custody is important as an evidentiary matter in lawsuits and employment dismissal proceedings. In the past, when the urine bottle is sealed, a label having identification information is adhesively fastened to the cap of the urine bottle and the bottle itself. This procedure requires extra caution in the proper coding of the adhesive strip. It requires additional time and effort in the urine collection proceedings. It is also not tamper evident. Many times these labels fall off the bottles or have loose ends on either the cap or the bottle. As such, the potential exists for the cap to be removed from the bottle and placed on a different specimen bottle.

A common type of urine specimen bottle presently used has a pointed end in the body opposite the cap. This common type of urine bottle also contains just forty cubic centimeters of urine. The mouth of the bottle is quite narrow (twenty-eight centimeters). Additionally, there are markings formed on the interior of the bottle indicative of the level of the fluid within the bottle. At present, this bottle is unsatisfactory for many usages. Recently released military regulations require laboratory specimens of sixty cubic centimeters. Additionally, there is no technique in this common form of urine bottle for the maintenance of "chain of custody". It is also quite difficult to read the graduated markings formed on the interior of the bottle. Finally, the pointed end makes it very difficult to maintain the specimen upright for shipment, storage, or usage.

Another common type of urine specimen bottle is identified as a "Wheaton Bottle". The Wheaton Bottle has a proper size for military requirements, but lacks the other important features required for proper usage. Once again, there is a lack of ability to maintain the "chain of custody". The curvature of the ring on the neck of the bottle makes it inappropriate and unusable in combination with tamper-resistant caps. Additionally, there are no graduated markings on the bottle to assist the urine collector in obtaining proper specimens.

It is an object of the present invention to provide a urine bottle that has a threaded surface on the neck of the bottle suitable for the attachment of tamper-resistant caps.

It is another object of the present invention to provide a urine bottle that includes a tamper-evident closure.

It is another object of the present invention to provide a urine bottle having a suitable size, with suitable markings, for the convenient collection of urine specimens.

It is still a further object of the present invention to provide a urine bottle that enhances the ability to prove chain of custody.

It is still another object of the present invention to provide a urine bottle that can be maintained in an upright position.

These and other objects and advantages of the present invention will become apparent from a reading of the attached specification and appended claims.

SUMMARY OF THE INVENTION

The present invention is a urine bottle comprising a bottle having a closed bottom portion and a neck portion integrally formed with the body. The neck portion has an outwardly formed ring having a flat lower edge. The neck portion has an exterior thread formed above the ring. The neck portion defines the mouth of the bottle. The mouth opens to the interior of the bottle.

The body has a generally cylindrical shape. The bottom portion is bowed inwardly from the body. The body has a plurality of graduated markings formed on the exterior of the body. These graduated markings are indicative of the volume of fluid within the body. These graduated markings include a bold marking formed on the body indicative of the sixty cubic centimeter volume of fluid in the body. The body has an overall internal volume of ninety cubic centimeters of fluid.

The neck portion is annular and has a diameter less than the internal diameter of the body. Specifically, the mouth has a diameter of thirty-eight millimeters.

A cap is threadedly connected to the exterior thread on the neck portion. This cap forms a liquid-type seal against the mouth. The cap has identification information printed on the top surface of the cap. The cap has a detachable collar extending about the bottom of the cap. This detachable collar separates from the cap upon the removal of the cap from the neck portion. This detachable collar has plurality of inward flaps extending from the bottom of the collar. These flaps engage the flat lower edge of the ring. Specifically, these flaps have an inward upper edge abutting the flat lower edge of the ring. The detachable collar is connected to the cap by a plurality of thin plastic extensions. Upon the detaching of the detachable portion from the bottle, the extensions sever. The cap also has a mechanical fluid-resistant seal integrally formed in the upper inner edge of the cap. In use, the mechanical seal abuts the mouth and causes a liquid-tight seal to be formed.

BEST MODE FOR CARRYING OUT THE INVENTION

Figure 1:
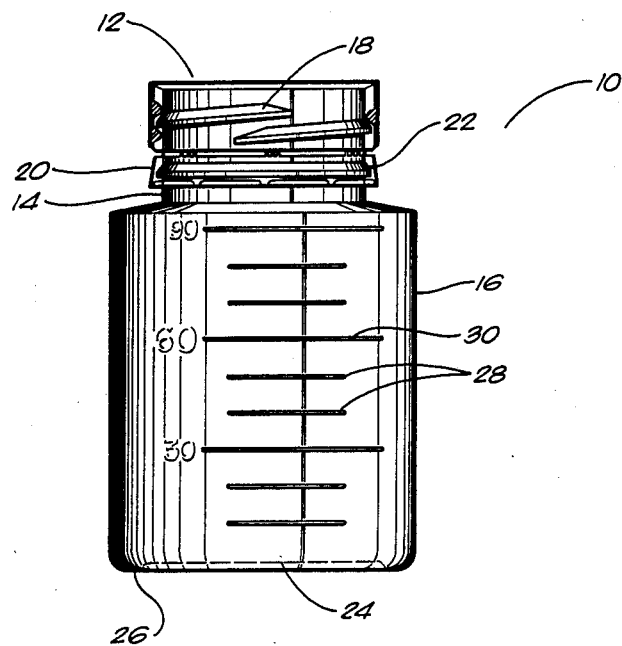
FIG. 1 shows the urine bottle of the present invention in side elevation with cap attached.

Referring to FIG. 1, there is shown the urine bottle 10 in accordance with the preferred embodiment of the present invention. The urine bottle 10, as shown in FIG. 1 has the cap 12 attached to the neck portion 14 of the body 16. Each of these components interact so as to form the improved urine bottle of the present invention.

It can be seen in FIG. 1, that the cap 12 is threadedly attached to the exterior thread 18 on the neck portion 14 of body 16. The cap 12 includes a detachable portion 20 located at the bottom of the cap 12. The detachable portion 20 engages an outwardly formed ring 22 having a flat lower edge. The interaction of the ring 22 and the detachable portion 20 serves to securely adhere the detachable portion 20 to the neck 14 of the urine bottle 10.

The body 16 has a closed bottom portion 24. The closed bottom portion 24 is bowed inwardly into the body 16. A flat edge surface 26 of body 16 allows the body 26 to be securely positioned on any flat surface. In the molding process, a small nipple, or other deformation, may occur in the area of bottom 24. Such a deformation in this area could cause the bottle 10 to tilt relative to a flat bottom surface or to be out of balance. The configuration of the bottom 24 of bottle 16 enhances the stability of the bottle when placed on a flat surface.

Urine bottle 10, shown in FIG. 1, has a plurality of graduated markings 28. These graduated markings are formed on the exterior surface of the body 16. These graduated markings 28 are indicative of the volume of fluid within the body 16. It is important that the markings 28 be placed on the exterior of the bottle. First, these exterior markings are more easily viewed than the formed interior markings on prior art urine bottles. Secondly, the formation of these markings on the exterior of the bottle allows a person to have a more accurate "feel" of the level of fluid, and the desired level of fluid, within the bottle 10. A bold marking 30 is formed on the body so as to be indicative of the sixty cubic centimeter volume of fluid within the body. This bold marking is important because of recent military requirements. In particular, in drug testing in the military, it is necessary to provide a sixty cubic meter sample of urine to the examining laboratory. This bold marking gives the person an accurate indicator of this requirement. Otherwise, many samples having insufficient volume may be shipped to the laboratory for testing.

The overall internal volume of the body 16 is approximately ninety cubic centimeters. The ninety cubic centimeters of fluid allows a suitable overflow margin and provides a suitable specimen to the examining laboratory. A greater amount of fluid than ninety centimeters would increase shipping costs and would be much more than was required for suitable urine testing. A lesser amount than ninety cubic centimeters would reduce the margin of error when attempting to reach the sixty cubic centimeter level.

Figure 2:
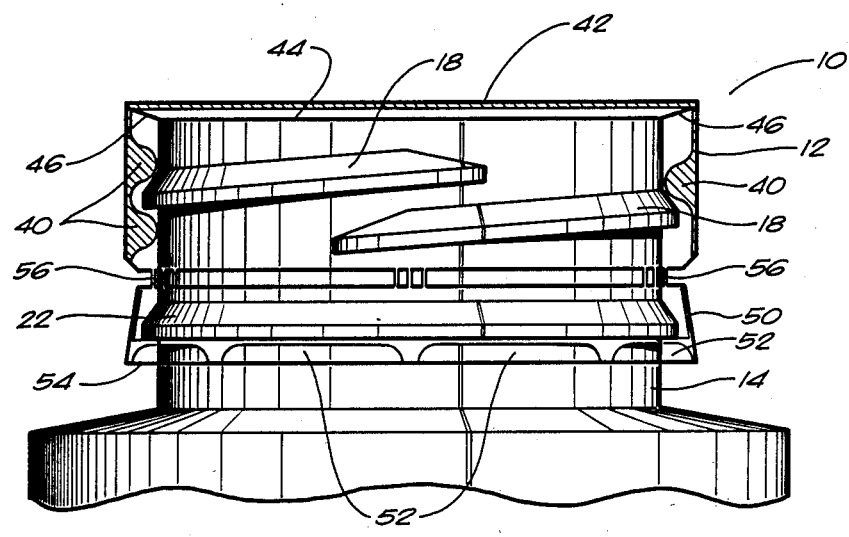
FIG. 2 is a closeup view in cross-section of the attachment between the cap and the neck of the bottle.
Figure 5:
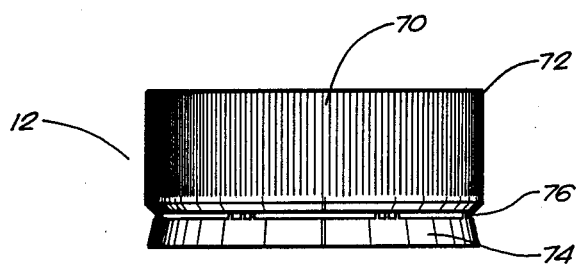
FIG. 5 is a side view showing the cap of the urine bottle.
Figure 6:
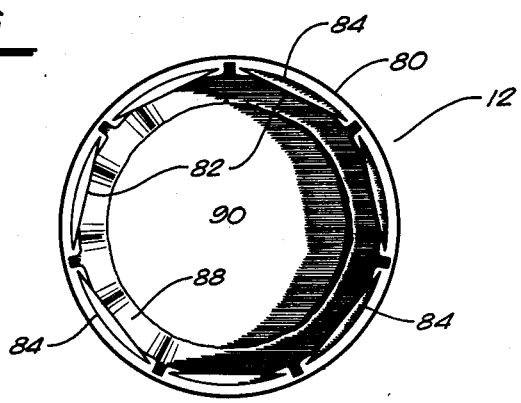
FIG. 6 is a bottom view of the cap of the present invention.
Figure 7:
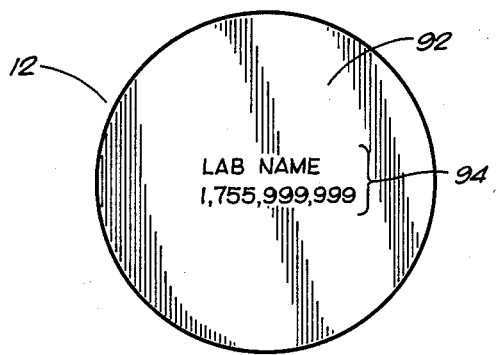
FIG. 7 is a top view of the cap of the urine bottle of the present invention.

FIG. 2 is a closeup view of the manner in which the cap 12 engages the neck portion 14 of the urine bottle 10. A more detailed description of the cap 12 is shown in FIGS. 5-7. Importantly, the method of attaching the cap 12 to the urine bottle 10 is an important consideration of the present invention. The cap 12 is threadedly connected to the exterior thread 18. Exterior thread 18 is formed outwardly from the surface of neck 14. This exterior thread 18 is a single spiral thread that serves to engage the internal thread 40 formed on the interior of cap 12. The top 42 of cap 12 extends across the mouth 44 of the neck portion 14 in relatively close abutment. A mechanical fluid-resistant seal 46 is integrally formed in the upper inner edge of the cap 12. This mechanical seal 14 abuts the mouth 44 of the neck portion 14 so as to maintain a liquid-type seal between the cap 12 and mouth 44.

Cap 12 has a detachable collar 50 extending about the bottom of the cap 12. The purpose of this detachable collar 50 is to separate from the cap 12 upon the threaded removal of the cap 12 from the neck portion 14 of urine bottle 10. Detachable collar 50 has a plurality of inward flaps 52 extending from the bottom edge 54 of detachable collar 50. As can be seen, the upper edge of these flaps 52 engages the flat lower edge of ring 22. As stated previously, ring 22 is formed outwardly from the surface of neck portion 18 and has a flat lower edge. It is important that this ring 22 have a flat lower edge in order to properly receive the top surface of flaps 52. A curved lower edge would be unsuitable since the flaps 52 would tend to slide over and off the ring 22. By having the flat lower edge on ring 22, it becomes very difficult to remove the detachable ring 50 from the neck portion 14 of urine bottle 10.

The detachable collar 50 is connected to the upper cap 12 by a plurality of thin plastic extensions 56. Thee extensions break upon the detaching of the detachable portion from the cap 12.

Figure 3:
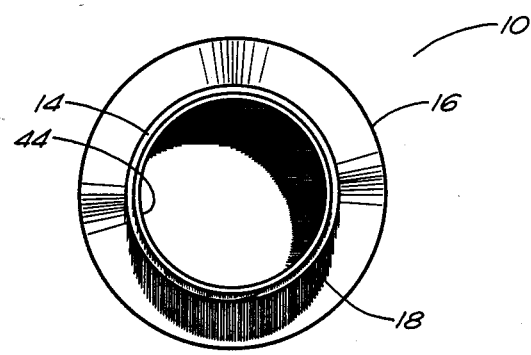
FIG. 3 is a top view of the bottle without the cap attached.

FIG. 3 is a top view of the urine bottle 10 without the cap. As can be seen, the urine bottle 10 has a circular cross-section and a generally cylindrical shape. It can be seen from FIG. 3 that the diameter of the body 16 is greater than the diameter of the neck portion 14. The mouth 44 has a diameter of thirty-eight millimeters. In the development of the present invention, the thirty-eight millimeter diameter is considered important in view of the prior art urine bottles. Many prior art urine bottles have a relatively small mouth. As such, there is much difficulty in filling the urine bottle with a specimen and there is much risk of spilling. The purpose of the small thirty-eight millimeter opening is to accommodate the standard caps that are on the market. The present invention overcomes these problems by offering a cap suitable for proper sealing attachment with a much wider opening on the urine bottle. The present invention, by its thirty-eight millimeter opening, is easier to fill, easier to ship without spilling, and easier to seal. In contrast with prior urine bottles, the present invention, by having a narrowing neck (relative to the fluid containing body) reduces the chance of urine sloshing from the bottle or accidentally spilling from the bottle. This benefit is further enhanced by the secure bottom surface of the body of the urine bottle.

Figure 4:
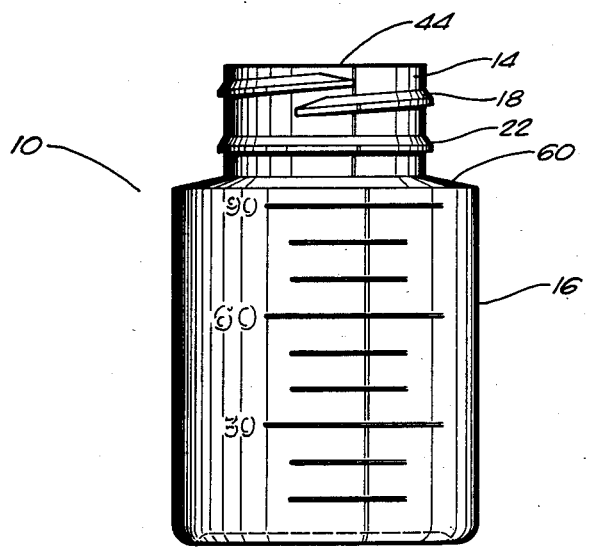
FIG. 4 is a side elevational view of the urine bottle of the present invention.

FIG. 4 is a side view of the urine bottle 10 without the cap attached. Specifically, FIG. 4 shows the neck portion 14 as integrally formed with the body portion 16. Suitable sloping shoulders 60 connect the bottom edge of the neck portion 14 with the body portion 16. The sloping shoulder 60 serves to dampen the movement of the fluid within the body and serves to prevent the sloshing of the fluid. It can be seen in FIGS. 3 and 4 that the neck portion 14 defines the mouth 44. Neck portion 14 is generally annular and has exterior threads 18 and ring 22 formed thereon.

FIG. 5 is an exterior view of the side of the cap 12. It can be seen that cap 12 has a plurality of vertical grip lines 70. The grip lines 70 enhance the ability of the user of the urine bottle to fasten the top to the bottle and to remove the top from the bottle. This is important because of the need to detach the upper portion 72 from the detachable collar 74. A smooth exterior surface on cap 12 would make such detachment more difficult. It can be further seen in FIG. 5 that the detachable collar 74 is connected by plastic extensions 76 to this upper portion 72.

FIG. 6 is a bottom view showing the interior configuration of the cap 12. In FIG. 6, it can be seen that the flaps 80 extend radially inwardly from the edge of the detachable collar 74. The inner edge 82 of these flaps 80 engage the flat lower edge of the ring formed on the exterior of the neck portion 14 of the urine bottle. These flaps 80 should have sufficient strength to withstand the forces required to sever the plastic extensions 76. Flanges 84 are integrally formed on these flaps 80 to strengthen the flap and to provide the necessary structural integrity. FIG. 6 also shows the rough circular configuration of the mechanical fluid-resistant seal 88 formed in and extending from the upper inner edge of the cap 12. As stated previously, this mechanical seal 88 provides the liquid-tight seal between the inside surface 90 of the top of the cap 12 and the mouth of the urine bottle.

FIG. 7 shows the top of cap 12. Specifically the top 92 has a flat surface. On this surface, identification information 94 is laser-encoded. Specifically, this identification information 94 includes a seven digit number representing the lab name and a serialized code between 1 and 176,000,000. The serialized code will represent the specific sample coming from such laboratory.

The present invention offers a number of improvements over the prior art urine bottles. Specifically, the laser encoding of identification information 94 onto the top surface of the cap 12 enhances the ability to trace the chain of custody. In normal practice, the urine specimen will be placed into the bottle and the cap closed onto the bottle. In the present invention, once the cap is placed onto the bottle, it will become tamper-evident. When the cap 12 is placed onto the urine bottle, then the identification information 94 will be present on the top of the bottle. At such time, the identification information can be written or otherwise recorded in correlation with the person providing the specimen and with the clinic taking the specimen. From the time that the urine bottle 10 leaves the clinic until it is received by the laboratory, there is no question as to chain of custody. If the bottle arrives in the laboratory with the seal unbroken, then no change of custody has occurred. On the other hand, if the detachable collar has been separated from the cap, then the specimen will be invalid and another one required. The present invention offers a foolproof method of assuring that any specimen tampering will be visible to those receiving the original specimen.

The present invention is better able to accommodate the military requirements by offering a urine bottle that has the suitable capacity. The ability to comply with the military requirements is further enhanced by the bold sixty cubic centimeter marking and by the exterior graduations.

The present invention enhances the ability to ship urine by providing a urine bottle having a flat stable bottom and by providing a bottle that can be transported in an upright position. Prior to the present invention, urine specimens were typically shipped by placing the pointed-end urine bottle in an envelope. Disaster commonly occurred whenever the caps to the bottles were not sealed completely. The present invention, on the other hand, allows all of the urine specimens taken during a sampling to be placed upright in a box. This allows the urine specimens to be shipped with a minimal risk of spillage. The configuration of the bottle and the cap further protects against spillage.

The serialized code on the urine bottle enhances the ability to preserve confidentiality of the specimen. Since the laboratory identifies the specimen with a serialized code, there is no need for names or other information to be revealed to the laboratory during the testing procedure. All test results can be reported to the clinic by way of cross-referencing to the serialized code imprinted on the cap of the bottle.

The embodiments as illustrated and discussed in the specification are intended only to teach those skilled in the art the best way known by the inventor to make and use the invention. Nothing in the specification should be considered as limiting the scope of the present invention. Many changes could be made by those skilled in the art to produce equivalent systems without departing from the invention. The present invention should only be limited by the following claims and their legal equivalents.

I claim:

1. A urine bottle comprising:

a body having a closed bottom portion;

a neck portion integrally formed with said body, said neck portion having an outwardly formed ring having a flat lower edge, said neck portion having an exterior thread formed above said ring, said neck portion defining the mouth of said bottle, said mouth opening to the interior of said body; and a cap threadedly connected to said exterior thread of said neck portion, said cap forming a liquid-tight seal against said mouth, said cap having a serialized code integrally formed into the top surface of said cap, said cap having a detachable collar formed at the bottom of said cap, said detachable collar separating from said cap upon the removal of said cap from said neck portion.

2. The bottle of claim 1, said body having a generally cylindrical shape, said bottom portion bowed inwardly of said body.

3. The bottle of claim 2, said body having a plurality of graduated markings formed on the exterior of said body, said graduated markings indicative of the volume of fluid in said body.

4. The bottle of claim 3, said graduated markings comprising:
a bold marking formed on said body indicative of sixty cubic centimeter volume of fluid in said body.

5. The bottle of claim 2, said body having an internal volume of ninety cubic centimeters of fluid.

6. The bottle of claim 1, said neck portion being annular and having a diameter of less than the internal diameter of said body.

7. The bottle of claim 6, said mouth having a diameter of thirty-eight millimeters.

8. The bottle of claim 1, said detachable collar having a plurality of inward flaps extending from the bottom of said collar, said flaps engaging the flat lower edge of said ring.

9. The bottle of claim 8, said flaps having an inward upper edge abutting the flat lower edge of said ring.

10. The bottle of claim 1, said detachable collar connected to said cap by a plurality of thin plastic extensions, said extensions breaking upon the detaching of said detachable collar.

11. The bottle of claim 1, said cap having a mechanical fluid resistance seal integrally formed in the upper inner edge of said cap, said mechanical seal abutting said mouth.

12. A urine bottle comprising:
a body having an internal volume for receiving urine specimens;
a neck portion integrally formed with said body, said neck portion defining the mouth of said urine bottle, said neck portion having an exterior thread extending therearound; and
a cap threadedly connected to said exterior thread of said neck portion, said cap forming a liquid-tight seal against said mouth, said cap including a detachable collar formed at the bottom of said cap, said detachable collar separating from said cap upon the removal of said cap from said neck portion, said cap having a serialized code indelibly imprinted and integrally formed into the top surface of said cap.

13. The bottle of claim 12, said neck portion further comprising:
a ring formed outwardly of said neck portion, said ring having a flat lower edge.

14. The bottle of claim 13, said detachable collar having a plurality of inward flaps extending upwardly from the bottom of said collar, said flaps engaging said flat lower edge of said ring.

15. The bottle of claim 13, said mouth having a diameter of thirty-eight millimeters, said exterior thread formed between said mouth and said ring.

16. The bottle of claim 12, said body having a plurality of graduated markings formed on the exterior of said body, said graduated markings indicative of the volume of fluid in said body.

17. The bottle of claim 12, said body having an integrally formed sealed bottom, said bottom bowed inwardly of said body.

* * * * *